(12) United States Patent
Endo

(10) Patent No.: US 9,733,115 B2
(45) Date of Patent: Aug. 15, 2017

(54) ANALYZER, AND METHOD OF DETECTION LIQUID LEVEL IN AN ANALYZER

(71) Applicant: Sysmex Corporation, Kobe-shi, Hyogo (JP)

(72) Inventor: Takayuki Endo, Kobe (JP)

(73) Assignee: SYSMEX CORPORATION, Hyogo (JP)

( * ) Notice: Subject to any disclaimer, the term of this patent is extended or adjusted under 35 U.S.C. 154(b) by 148 days.

(21) Appl. No.: 14/665,614

(22) Filed: Mar. 23, 2015

(65) Prior Publication Data

US 2015/0268230 A1 Sep. 24, 2015

(30) Foreign Application Priority Data

Mar. 24, 2014 (JP) .................................. 2014-060393

(51) Int. Cl.
| | |
|---|---|
| *G01N 33/53* | (2006.01) |
| *G01F 23/00* | (2006.01) |
| *G01F 23/26* | (2006.01) |
| *G01N 35/10* | (2006.01) |
| *G01N 35/00* | (2006.01) |

(52) U.S. Cl.
CPC ............ *G01F 23/00* (2013.01); *G01F 23/265* (2013.01); *G01F 23/266* (2013.01); *G01F 23/268* (2013.01); *G01N 35/1011* (2013.01); *G01N 35/1004* (2013.01); *G01N 2035/00891* (2013.01); *G01N 2035/1018* (2013.01); *G01N 2035/1025* (2013.01)

(58) Field of Classification Search
CPC G01F 23/00; G01N 35/1011; G01N 35/1004; G01N 2035/1018; G01N 2035/1025; G01N 35/10; G01N 35/1002; G01N 35/1009; G01N 2035/0491; B01L 3/02; B01L 3/021; B01L 3/0224; B01L 3/0237
See application file for complete search history.

(56) References Cited

U.S. PATENT DOCUMENTS

| 4,451,433 A | * | 5/1984 | Yamashita | ....... G01N 35/00663 422/509 |
|---|---|---|---|---|
| 4,970,468 A | * | 11/1990 | Ishizawa | ............... G01F 23/263 324/662 |

(Continued)

FOREIGN PATENT DOCUMENTS

| JP | H11-271319 A | 10/1999 |
|---|---|---|
| JP | 2002-277475 A | 9/2002 |

(Continued)

*Primary Examiner* — Brian R Gordon
(74) *Attorney, Agent, or Firm* — Brinks Gilson & Lione

(57) ABSTRACT

The present invention improves the technology for detecting the level of a reagent in a container using changes of the capacitance, for instance, of an aspiration tube for aspirating the reagent from the container. The present invention can eliminate noises to detection of the capacitance caused by metals surrounding the container and changes of the moving speed of aspiration tube. Changes of the capacitance are detected using an empty container and recorded. The recorded changes are subtracted from changes of the capacitance measured with a container containing a reagent to eliminate the noises to the detection of changes of the capacitance.

18 Claims, 13 Drawing Sheets

(56) References Cited

U.S. PATENT DOCUMENTS

| | | | | | |
|---|---|---|---|---|---|
| 5,753,512 | A | * | 5/1998 | Riall | G01N 35/04 422/549 |
| 8,726,745 | B2 | * | 5/2014 | Heinze | G01F 23/2962 422/501 |
| 8,852,530 | B2 | * | 10/2014 | Oonuma | G01N 35/10 422/517 |
| 8,858,718 | B2 | * | 10/2014 | Gifford | B08B 3/044 134/1 |
| 8,911,685 | B2 | * | 12/2014 | Watanabe | G01F 23/00 422/501 |
| 8,936,765 | B2 | * | 1/2015 | Sarwar | G01N 35/1011 324/662 |
| 2005/0092080 | A1 | * | 5/2005 | Harazin | G01F 23/26 73/290 R |
| 2006/0093525 | A1 | * | 5/2006 | Brunner | G01F 23/2965 422/509 |
| 2010/0111767 | A1 | * | 5/2010 | Yonekura | G01N 35/026 422/65 |
| 2010/0210007 | A1 | * | 8/2010 | Iwamura | G01N 35/1011 435/286.2 |
| 2010/0290950 | A1 | * | 11/2010 | Nakaya | G01N 35/00594 422/67 |
| 2011/0318845 | A1 | * | 12/2011 | Kurono | G01N 35/00732 436/174 |
| 2013/0137087 | A1 | * | 5/2013 | Wilson | B01L 3/5085 435/5 |
| 2013/0183198 | A1 | * | 7/2013 | Tokunaga | G01N 21/59 422/68.1 |
| 2016/0313362 | A1 | * | 10/2016 | Sugiyama | G01N 35/1016 |

FOREIGN PATENT DOCUMENTS

| | | |
|---|---|---|
| JP | 2004-170279 A | 6/2004 |
| JP | 2007-322285 A | 12/2007 |
| JP | 2009-041961 A | 2/2009 |
| JP | 2011-013005 A | 1/2011 |
| JP | 2013-068432 A | 4/2013 |

\* cited by examiner

ANALYZER, AND METHOD OF DETECTION LIQUID LEVEL IN AN ANALYZER

CROSS REFERENCE TO RELATED APPLICATIONS

This application claims priority to Japanese Patent Application No. 2014-060393, filed on Mar. 24, 2014, entitled "ANALYZER, AND METHOD OF DETECTION LIQUID LEVEL IN AN ANALYZER", the entire contents of which are incorporated herein by reference.

FIELD OF THE INVENTION

The present invention relates to an analyzer, and a method of detecting a liquid level in an analyzer. More specifically, the present invention relates to an analyzer, and a method of detecting a liquid level in an analyzer capable of accurately detecting the level of a liquid such as a sample or a reagent stored in a container and aspirated therefrom by an aspirating tube.

BACKGROUND

Conventional sample analyzers are known to dispense samples such as blood or urine from sample containers to reaction vessels where a sample is mixed with a reagent for use in conducting an intended measurement, and then perform various types of measurements and analyses. The liquids, such as samples and reagents, used in such sample analyzers are stored in predetermined containers and aspirated by an aspirating tube which is inserted into a respective container. There is known art for minimizing the depth of insertion of the nozzle in the liquid to prevent contamination by detecting the liquid level in the container (refer to Japanese Laid-Open Patent Application No. H11-271319).

The art disclosed in Japanese Laid-Open Patent Application No. H11-271319 detects changes in an electrostatic capacity between the liquid and the aspirating tube to detect the liquid level within the container. The art is also configured to have removed static electricity charged on the container to suppress such static electricity from causing an inaccurate detection of the liquid level.

However, there are several factors to be considered other than static electricity that cause an inaccurate detection of the liquid level. For example, in an analyzer, such as the one disclosed in H11-271319, in which the liquid level is detected from detections of changes in electrostatic capacity, conductors such as metal panels and screws provided around the container can act as electrodes to greatly influence readings of the electrostatic capacity, resulting in that detected changes in electrostatic capacity due to travel of the aspirating tube through nearby conductors obscure a reading of the change in electrostatic capacity due to contact with the liquid and make harder the accurate detection of the liquid level. There also is a concern that a liquid level detection may also become inaccurate because of changes in the detected electrostatic capacity caused by a loosened metal screw present around the container and by a replaced metal part. There is further a concern that when liquid level detection is performed by a voltage sensor, a liquid level detection may be inaccurate because of changes in a detected voltage caused by differences in the shapes of containers holding the liquid. Hence, the environment surrounding the liquid level sensor greatly affects the detection signal of the liquid level sensor.

SUMMARY OF INVENTION

The scope of the present invention is defined solely by the appended claims, and is not affected in any way by the statements included in this summary.

A first aspect of the present invention is an analyzer comprising: a container holder configured to hold a container containing a liquid; an aspirating tube configured to aspirate the liquid from the container held by the container holder; a drive part configured to transfer the aspirating tube; a detector configured to output a signal based on a physical characteristic exhibited in relation between the aspirating tube and a liquid surface in the container; and a memory that stores, as a reference signal, the signal output from the detector when the aspirating tube is being transferred under a condition that the container containing the liquid which can be aspirated by the aspirating tube is not being held by the container holder; and a controller programmed to detect a liquid level in the container, based on the reference signal and a real signal output by the detector when the aspirating tube is transferred for an aspiration operation of the liquid.

A second aspect of the present invention is an analyzer comprising: a container holder configured to hold a container containing a liquid; an aspirating tube configured to aspirate the liquid from the container held by the container holder; a drive part configured to transfer the aspirating tube; a controller programmed to control the drive part; a detector configured to output a signal based on a physical characteristic exhibited in relation between the aspirating tube and a liquid surface in the container; and a memory that stores the signal output by the detector; wherein the controller is programmed to; store, as a reference signal in the memory, the signal output by the detector when the aspirating tube is being transferred under a condition that the container containing the liquid which can be aspirated by the aspirating tube is not being held by the container holder; and detect the liquid level in the container, based on the reference signal and a real signal output by the detector when the aspirating tube is transferred for an aspiration operation of the liquid.

A third aspect of the present invention is a method of detecting a liquid level in an analyzer comprising: a step of transferring an aspirating tube to aspirate a liquid from a container held in a container holder; a step of outputting, as a real signal, a signal based on a physical characteristic exhibited in relation between the aspirating tube and a liquid surface in the container, when the aspirating tube is being transferred for an aspiration operation of the liquid; and a step of detecting the liquid level in the container based on the real signal and a reference signal that is based on a physical characteristic exhibited in relation between the aspirating tube and the liquid surface in the container when the aspirating tube is being transferred under a condition that the container containing the liquid which can be aspirated by the aspirating tube is not being held by the container holder.

DETAILED DESCRIPTION OF THE PREFERRED EMBODIMENTS

Figure 1:
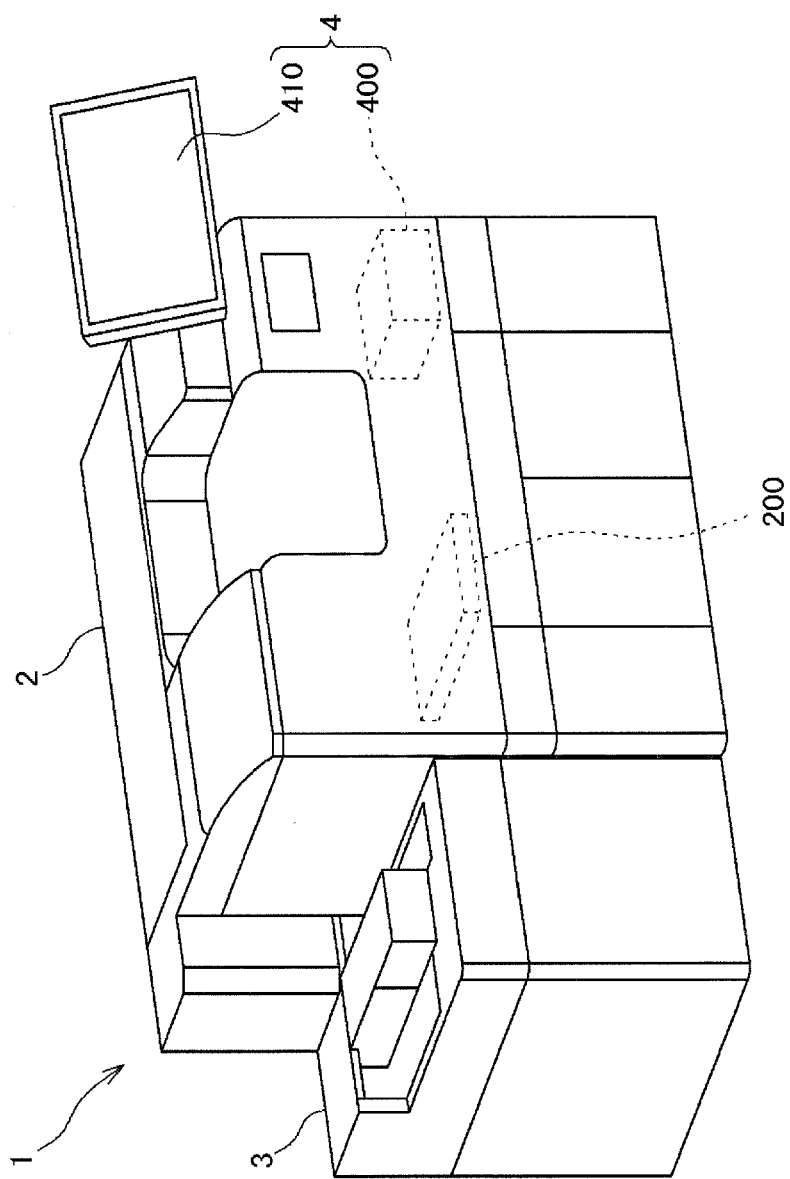
FIG. 1 is a perspective view showing a general structure of an immunoanalyzer 1 as an embodiment of the sample analyzer.

The preferred embodiments will be described hereinafter with reference to the drawings.

[General Structure of Immunoanalyzer 1]

An immunoanalyzer 1 performs various tests, such as a detection of hepatitis type-B, hepatitis type-C, tumor marker, and thyroid hormone contained in a plasma sample (hereinafter referred to simply as "a sample") by utilizing an antigen/antibody reaction. The immunoanalyzer 1 has a measuring section 2, a sample transporting section 3, and a control device 4. The measuring section 2 is connected to the sample transporting section 3 and the control device 4 for communication. The sample transporting section 3 is configured to transport a rack holding a plurality of test tubes containing samples collected from subjects. The control device 4 has a main body 400 and a display/input section 410. The display/input section 410 has a touch panel, and incorporates a display section and an input section.

Figure 2:
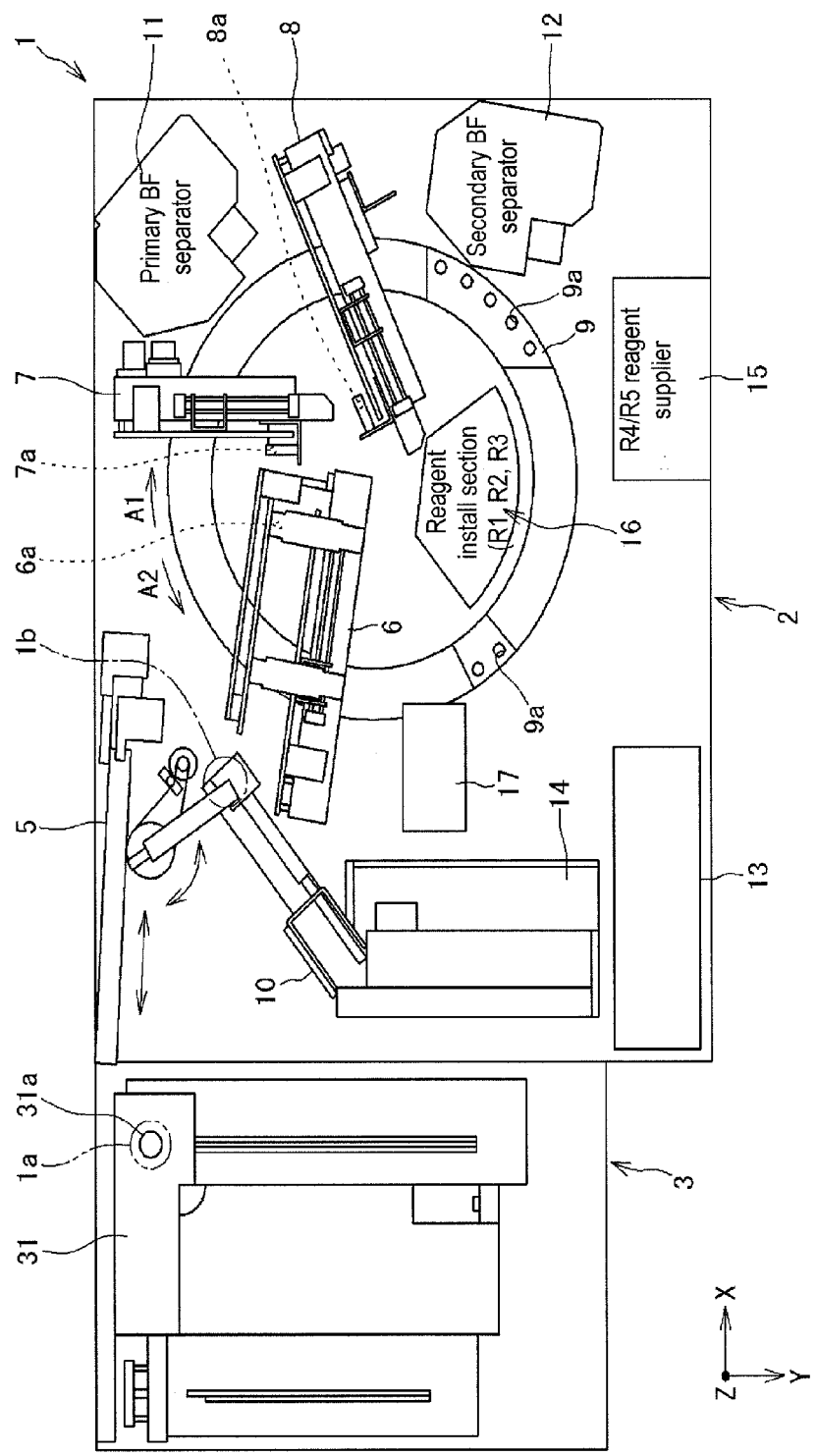
FIG. 2 is a plan view of the immunoanalyzer of FIG. 1.

As shown in FIG. 2, the measuring section 2 includes a sample dispenser 5, a R1 reagent dispenser 6, a R2 reagent dispenser 7, a R3 reagent dispenser 8, a reactor 9, a cuvette supplier 10, a Primary BF separator 11, a secondary BF separator 12, a pipette tip supplier 13, a measuring unit 14, a R4/R5 reagent supplier 15, a reagent installation section 16, a disposal unit 17, and a measurement controller 200 (see FIG. 1).

The sample transporting section 3 is configured to transport a rack holding a plurality of test tubes containing unprocessed samples.

In the immunoanalyzer 1, a sample to be measured is mixed with a buffer solution R1 reagent. The resulting liquid mixture is further mixed with an R2 reagent which contains magnetic particles carrying a capture antibody for binding to the antigen in the sample. The contents in the sample that are not bound to the capture antibody are separated when magnetic particles carrying the capture antibody bound to the antigen are attracted to a magnet (not shown in the drawing) of the primary BF (bound free) separator 11. After an R3 reagent containing a labeled antibody antibodies has been added, the magnetic particles carrying the capture antibody bound to the antigen and the labeled antibody are attracted to a magnet of the secondary BF separator 12 (not shown in the drawing) to separate the R3 reagent that contains the unreacted labeled antibody. After adding an R5 reagent containing a luminescent substrate, which luminesces via a reaction between the labeled antibody and the R4 reagent, which is a dispersion liquid, the amount of light produced by the reaction between the labeled antibody and the luminescent substrate is measured. The antigen contained in the sample bound to the labeled antibody can be quantified through this process.

The cuvette supplier 10 is configured to accommodate a plurality of cuvettes, and sequentially supplies the cuvettes one after another to the discharge position 1b.

An aspirating tube 6a for aspirating and discharging the R1 reagent is attached to the R1 reagent dispenser 6, as shown in the drawing. A pipette is used as the aspirating tube 6a in the present embodiment. The R1 reagent dispenser 6 aspirates the R1 reagent from the reagent container installed in the reagent installation section 16, and discharges the aspirated R1 reagent to a cuvette placed at the discharge position 1b using the aspirating tube 6a.

The pipette tip supplier 13 moves a plurality of loaded pipette tips (not shown in the drawing) one after another to the tip installation position (not shown in the drawing). Thereafter, a pipette tip is mounted on the pipette end of the sample dispenser 5 at a tip installation position.

The sample dispenser 5 aspirates the sample in the test tube moved to the sample aspirating position 1a by the sample transporting section 3 using the installed pipette tip. This aspiration operation is accomplished through a hole 31a formed in a cover 31 that covers the transport path of the sample transporting section 3. The sample dispenser 5 discharges the aspirated sample into a cuvette at the discharge position 1b. The R1 reagent was previously dispensed to the cuvette by the R1 reagent dispenser 6. Thereafter, the cuvette is moved to the reactor 9 by a catcher (not shown in the drawing) of the R1 reagent dispenser 6.

As shown in the drawing, an aspirating tube 7a for aspirating and discharging the R2 reagent is attached to the R2 reagent dispenser 7. A pipette is used as the aspirating tube 7a in the present embodiment. The R2 reagent dispenser 7 aspirates the R2 reagent from the reagent container installed in the reagent installation section 16, and discharges the aspirated R2 reagent to a cuvette containing the R1 reagent and the sample.

The reactor 9 is formed in an annular shape so as to circumscribe the reagent installation section 16, which is circular, as shown in the drawing. The reactor 9 has a plurality of cuvette holders 9a arranged at a predetermined spacing along the exterior. Cuvettes set in the cuvette holders 9a are heated to approximately 42° C. Hence, the heating promotes reaction of the various reagents and the sample in the cuvette. The reactor 9 is configured to be horizontally rotatable in the clockwise direction, and moves the cuvette set in the cuvette holder 9a to respective processing positions where various processes, such as dispensing reagent, are performed.

The cuvette containing the sample and the R1 and R2 reagents is moved by a catcher (not shown in the drawing) from the reactor 9 to the primary BF separator 11. A primary BF separation is performed by the primary BF separator 11. The contents in the sample that are not bound to the capture antibody of the R2 reagent are thus removed from the sample within the cuvette. After the primary BF separation is completed, the cuvette is returned to the reactor 9 by the catcher (not shown).

An aspirating tube 8a for aspirating and discharging the R3 reagent is attached to the R3 reagent dispenser 8, as shown in the drawing. A pipette is used as the aspirating tube 8a in the present embodiment. The R3 reagent dispenser 8 uses the aspirating tube 8a to aspirate the R3 reagent set at the reagent installation section 16. The R3 reagent dispenser 8 also uses the aspirating tube 8a to discharge the aspirated R3 reagent into the cuvette which was moved from the primary BF separator 11 to the reactor 9.

After the elimination process by the primary BF separator 11, the cuvette containing the R3 reagent and the sample already processed by the primary BF separator 11 is moved from the reactor 9 to the secondary BF separation section 12 by a catcher (not shown in the drawing). A secondary BF separation is performed in the secondary BF separator 12. The R3 reagent including unreacted labeled antibody is thereby eliminated. After the secondary BF separation is completed, the cuvette is returned to the reactor 9 by the catcher (not shown).

The R4/R5 reagent supplier 15 sequentially dispenses the R4 and R5 reagents to the cuvette containing the sample after the elimination process performed by the secondary BF separator 12 via a catcher not shown in the drawing.

The reagent installation section 16 holds a plurality of reagent containers which accommodate the R1 reagent, the R2 reagent, and the R3 reagent, respectively, for respective measurement items. The reagent installation section 16 also holds a container of BSA buffer as a sample buffering solution, which is used to dilute a sample when diluted sample measurements are performed.

The measuring unit 14 obtains light produced during the reaction process between the luminescent substrate and the labeling antibody bound to the antigen of the sample subjected to a predetermined process via a photomultiplier tube. The measuring unit 14 sends signals indicative of the amount of obtained light to the measurement controller 200 (refer to FIG. 1).

The disposal unit 17 is a unit for disposal of cuvettes and waste fluid within the cuvettes after detection is completed, and the disposal unit has an aspiration part (not shown) for aspirating waste fluid within the cuvette, and a disposal hole (not shown). After detection, the cuvette is moved from the measuring unit 14 to the disposal unit 17 by a catcher (not shown), and waste fluid within the cuvette is aspirated by the aspiration part, and the cuvette from which the waste fluid has been aspirated is discarded through the disposal hole in the disposal unit 17.

The measurement controller 200 of the measuring section 2 has a CPU and a memory comprised of a ROM, a RAM or the like. The measurement controller 200 is programmed to control each part of the measuring section 2 in accordance with signals output by the main body 400 of the control device 4 shown in FIG. 1. The controller 200 receives the signals sent from the measuring unit 14, converts the signals to measurement values, and analyzes the converted measurement values. The measurement controller 200 transmits the analysis results to the main body 400 of the control device 4.

Figure 3:
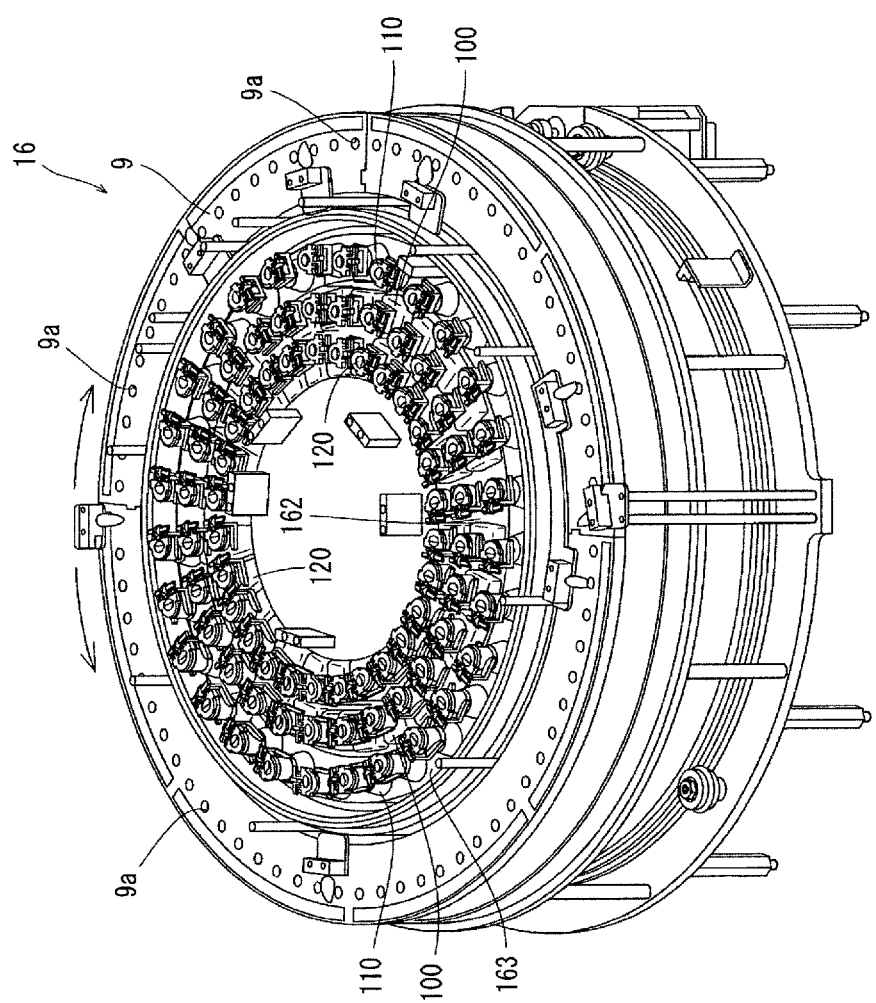
FIG. 3 is a perspective view of a reagent installation unit.

As shown in FIG. 3, the reagent installation section 16 includes an annular table 162 on its inner side, and an annular table 163 on the outer side, when viewed from above.

The inner table 162 has a plurality of container holders capable of holding the R1 reagent container 100 which contains the R1 reagent, and a plurality of container holders capable of holding the R3 reagent container 120 which contains the R3 reagent. These container holders accommodate a plurality of R1 reagent containers 100 on the inner side of the table 162 in an annular arrangement, and the R1 reagent containers 100 are circumscribed on the outer side by the R3 reagent containers 120, which are arranged along the circumference, as shown in the drawing.

The outer table 163 has a plurality of container holders capable of holding the R2 reagent container, which contains R2 reagent. These container holders accommodate R2 reagent containers 110 on the outside table 163 in an annular arrangement so as to circumscribe the R1 reagent containers 100 on the outer side, as shown in the drawing.

The inner table 162 and the outer table 163 are configured to be horizontally rotatable in the circumferential direction via step motors which are not shown in the drawing. The reagent containers 100, 110, and 120 placed in the container holders are disposed at the reagent aspirating position to aspirate the reagent through the reagent dispensers 6 through 8 by rotating the inner table 162 and the outer table 163.

Note that a cover which is not shown in the drawing is provided on the top surface of the reagent installation section 16 so as to cover both the reagent installation section 16 and the reactor 9, and an opening is formed in the cover to permit insertion therethrough of the aspirating tubes 6a-8a of the reagent dispensers 6-8.

Figure 4:
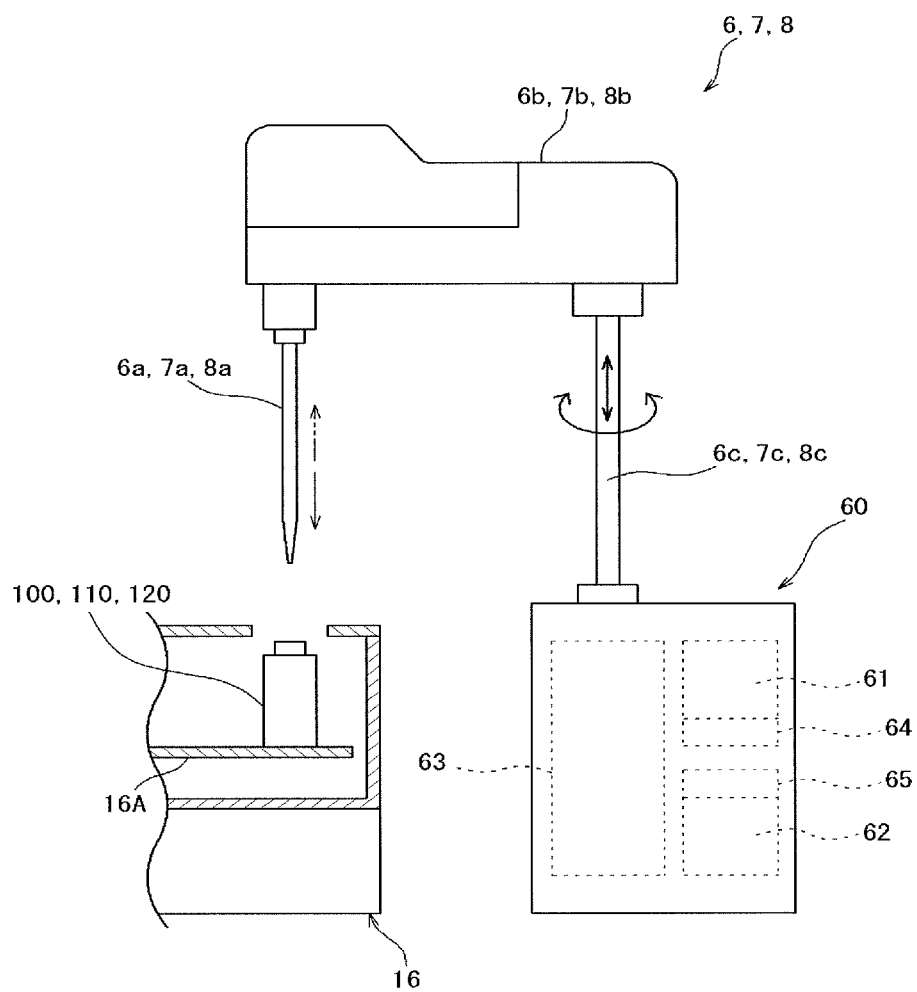
FIG. 4 is a side view briefly showing a structure of a reagent dispensing unit.

As shown in FIG. 4, the reagent dispensers 6-8 each have an arm 6b, 7b, 8b, a drive unit 60 configured to move the attached arm 6b, 7b, 8b vertically and rotate the arm 6b, 7b, 8b with a shaft 6c, 7c, 8c, and an aspirating tube 6a, 7a, 8a attached at the tip of the arm 6b, 7b, 8b to aspirate and discharge the reagent in reagent containers 100, 110, and 120 which are held in the container holder 16A of the reagent installation section 16.

The drive unit 60 has a rotation motor 61, an elevator motor 62, and a transmission unit 63 for transmitting the drive forces of the rotation motor 61 and the elevator motor 62 to the shaft. The transmission unit 63 is comprised of a belt transmission mechanism and a gear transmission mechanism or the like for reducing the rotational speed of the rotation motor 61 and transmitting the reduced rotation to the shaft 6c, 7c, 8c, and a belt transmission mechanism and a rack and pinion mechanism for converting the rotational force of the elevator motor 62 into vertical movements and transmitting the vertical movements to the shaft 6c, 7c, 8c. Encoders 64 and 65 are provided to output signals according to the degree of rotational displacement of the rotation motor 61 and the elevator motor 62, and the output signals of the encoders 64 and 65 are sent to the measurement controller 200. The measurement controller 200 detects the rotational positions and vertical positions of the aspirating tube 6a, 7a, 8a by counting the output signals of the encoders 64 and 65. The encoders 64 and 65 therefore constitute a position detection unit for detecting the position of the aspirating tube 6a, 7a, 8a. Note that alternative configurations may be available in place of the position detection unit, such as those directly detecting the positions of the aspirating tube 6a, 7a, 8a or using an optical sensor or the like to detect members which move in association with the aspirating tube 6a, 7a, 8a.

The measuring section 2 of the present embodiment also has, in addition to the various parts mentioned above, a liquid level detecting unit 20 (see FIG. 5) configured to detect a liquid level of the reagent in the reagent containers 100, 110, and 120 installed in the reagent installation section 16. The structure of the liquid level detecting unit 20 will be described below in detail.

As shown in FIG. 1, the control device 4 is comprised of a body part 400, and a display/input part 410. The body part 400 has a CPU, a memory part such as a ROM, a RAM, a hard disk, an I/O interface, and an image output interface.

The CPU of the body part 400 executes various programs installed in the memory part.

The I/O interface of the body part 400 receives signals output from the display/input section 410. An image output interface of the body part 400 outputs image signals representative of image data to the display/input part 410.

The display/input part 410 displays images based on the image signals received from the image output interface, and outputs instructions received from a user through the screen of the display/input part 410 to the I/O interface 406.

The communication interface of the body part 400 transmits signals from the body part 400 to the measurement controller 200 of the control section 2 and receives signals sent from the measurement controller 200.

Reagent Aspiration Operation of the Reagent Dispensing Unit

Figure 5:
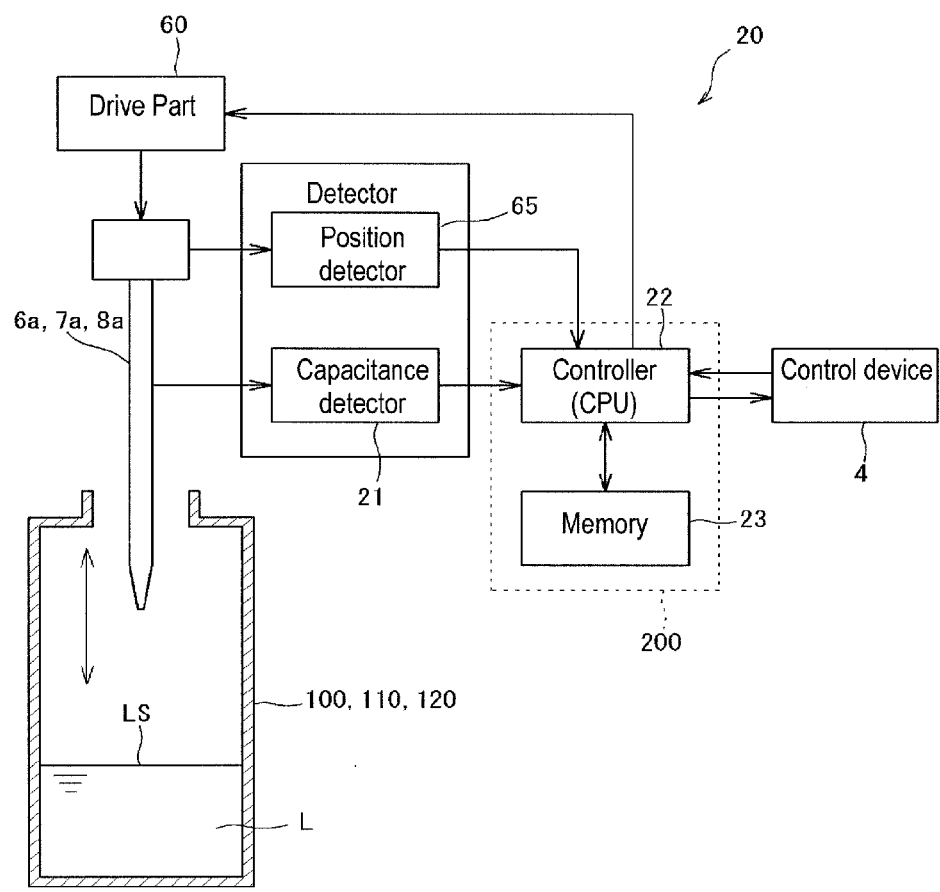
FIG. 5 is a block diagram showing a structure of a liquid level detector.

As shown in FIG. 5, the liquid level detecting unit 20 has a position detector 65 which detects the vertical positions of the aspirating tube 6a, 7a, 8a, a capacitance detector 21 which detects changes in the capacitance between the aspirating tube 6a, 7a, 8a and its surrounding environment, a controller 22 which receives output signals of the position detector 65 and the capacitance detector 21, detects a liquid surface LS of the reagent L, and controls the drive unit 60 in accordance with the detected liquid level, and a memory 23 which stores background signals used to detect the reagent liquid level. The controller 22 and memory 23 are comprised of a CPU and a memory of the measurement controller 200.

The position detector 65 is comprised of an encoder which outputs pulse signals indicative of rotation of the elevator motor 62 in the reagent dispenser 6, 7, 8, as previously described. An output of the position detector 65 is input to the controller 22.

Note that a configuration in which a step motor is used as the elevator motor 62 dispenses with the position detector 65 and enables a detection of the position by counting pulses of a drive signal applied to the elevator motor 62.

Figure 6:
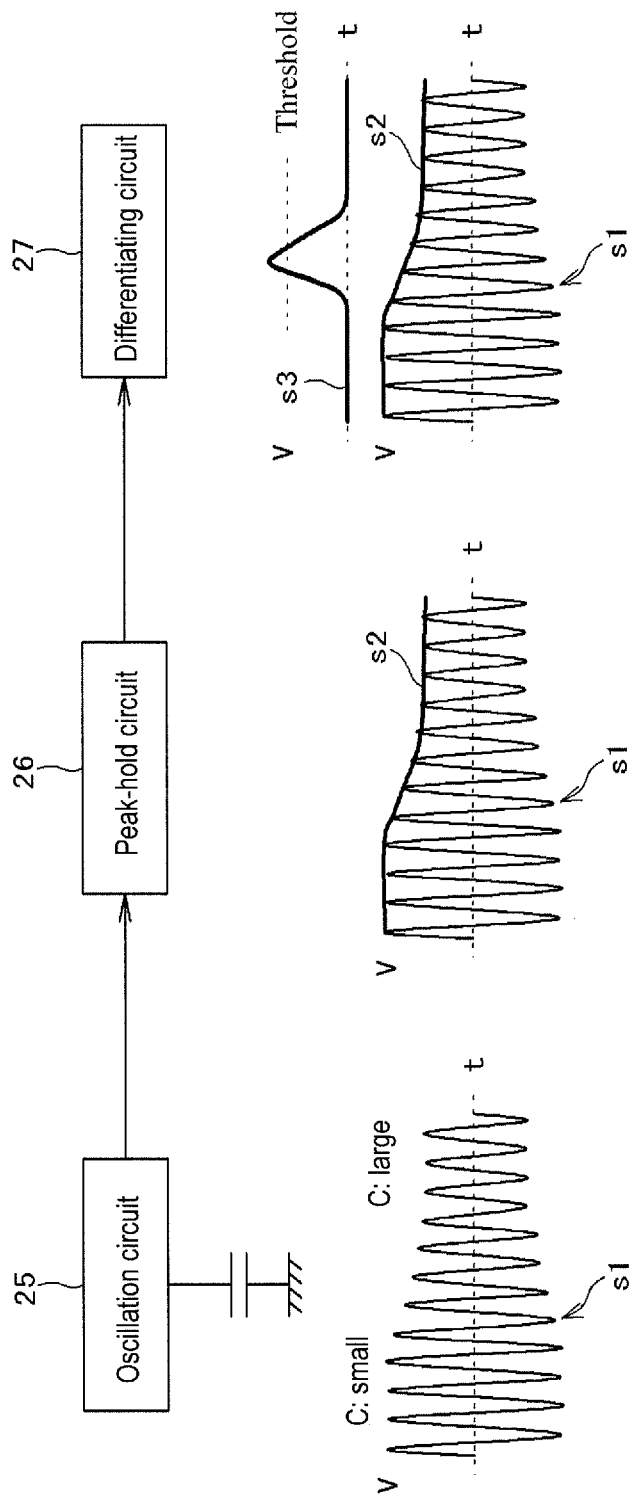
FIG. 6 is a block diagram showing a structure of a capacitance detector.

The capacitance detector 21 is a capacitance sensor which detects changes in the electrostatic capacity between the aspirating tube 6a, 7a, 8a and its surrounding conductors, such changes being caused by the vertical movements of the aspirating tube 6a, 7a, 8a. Specifically, the capacitance detector 21 incorporates an oscillation circuit 25 which oscillates at a high frequency, a peak-hold circuit 26 which contours the peak values of the oscillations from the oscillation circuit 25, and a differentiating circuit 27 which derives changes in of the peak values of the oscillations output from the peak-hold circuit 26, as shown in FIG. 6. Note that examples of the output signals s1, s2, and s3 of the circuits 25, 26, and 27 are shown in FIG. 6.

When the aspirating tube 6a, 7a, 8a is lowered, the capacitance changes because of changes in the distance between the aspirating tube 6a, 7a, 8a and the reagent liquid level in the reagent containers 100, 110, or 120, and the capacitance changes greatly when the aspirating tube 6a, 7a, 8a contacts the liquid surface. Changes in the capacitance manifest as changes in the amplitude of the output signal s1, which represents the output voltage of the oscillation circuit 25. Specifically, the amplitude of the output signal s1 of the oscillation circuit 25 increases when the capacitance becomes small, and the amplitude decreases when the capacitance increases.

The peak-hold circuit 26 contours the peak values of the output signal s1 of the oscillation circuit 25, which represent the magnitudes of the capacitance C and outputs this peak values to the differentiating circuit 27. Although the output signal s2 of the peak-hold circuit 26 represents the magnitude of the capacitance, changes thereof are slight. Therefore, a rate of changes in the output signal s2 of the peak-hold circuit 26 is obtained by the differentiating circuit 27. The output signal s3 of the differentiating circuit 27 therefore increases when the capacitance C changes rapidly because of the contact of the aspirating tube 6a, 7a, 8a with the liquid surface LS, and the contact between the liquid surface and the aspirating tubes 6a-8a can be detected in this way.

The output signal of the capacitance detector 21 is input to the controller 22. The controller 22 detects the level of the liquid surface LS of the reagent L from the output signal of the position detector 65 and the output signal of the capacitance detector 21. The controller 22 also controls the drive unit 60 to further lower the aspirating tube 6a, 7a, 8a to a position at which the reagent L can be aspirated based on the detected level of the liquid surface LS of the reagent L Although the reagent containers 100, 110 and 120 are installed in the reagent installation section 16, there are various conductive members such as metal panels and screws are installed at the reagent installation section 16 and at its surroundings. The output of the capacitance detector 21 is affected not only by the reagent L within the reagent containers 100, 110, and 120, but also by the conductors surrounding the aspirating tubes 6a-8a. Since the capacitance ripples as the aspirating tube 6a, 7a, 8a vertically moves through these nearby conductors, it becomes difficult to discern the change caused by a contact of the aspirating tube 6a, 7a, 8a with the liquid surface LS, and hence it becomes difficult to accurately detect the liquid surface LS. Since the capacitance exhibits rapid changes when the aspirating tube 6a, 7a, 8a accelerates or decelerates while moving vertically, it also becomes difficult to discern the change caused by a contact of the aspirating tube 6a, 7a, 8a with the liquid surface LS in this case.

The liquid level detecting unit 20 of the present embodiment is configured to accurately detect the liquid surface LS of the reagent L by taking into account changes in the capacitance caused by interactions between the aspirating tube 6a, 7a, 8a and its surrounding environment excluding the reagent L in the reagent containers 100, 110, and 120, as described below.

Specifically, when the reagent container 100, 110, 120 is empty of reagent or reagent is consumed to the point at which the reagent cannot be aspirated by the aspirating tube 6a, 7a, 8a, or when the reagent container 100, 110, 120 installed in reagent installation section 16 contains a reagent below the dead volume level, the controller 22 of the liquid level detecting unit 20 moves the aspirating tube 6a, 7a, 8a vertically and detects changes in the capacitance at positions of the aspirating tube 6a, 7a, 8a along the vertical travel. The controller 22 then stores this signal as the "background signal" (referred to as "reference signal" hereinafter) in the memory 23. In the present embodiment, the signal representing changes of the capacitance detected while the aspirating tube 6a, 7a, 8a is traveling is stored as the reference signal. The background signal is compared to the output signal of the capacitance detector 21 output when the reagent is actually aspirated from the reagent container 100, 110, 120 (referred to as "liquid level detection signal" or "real signal" hereinafter) to detect the liquid surface of the reagent L by eliminating the environmental influences around the reagent L.

Note that "while the aspirating tube 6a, 7a, 8a is traveling" refers to a time interval measured from the starting point of the aspirating tube (for example, the dead bottom point) to the arrival point (for example, the dead top point). The way the aspirating tube travels is not specifically limited as long as the tube moves from the starting point to the arrival point. For example, the tube may travel continuously or intermittently from the starting point to the arrival point.

Note that the background signal can be obtained and stored in the memory 23 just once when the immunoanalyzer 1 is manufactured or installed, or can be obtained and stored in the memory 23 automatically each time the power source of the immunoanalyzer 1 is turned on, that is, whenever the immunoanalyzer 1 is started. The output signal of the capacitance detector 21 changes when the metal parts are replaced or metal screws loosen which are installed around the containers. Therefore, in order to more accurately detect the liquid level, a time interval needs to be short between a time the background signal is acquired and a time the liquid level is detected. In the present embodiment, the background signal is automatically obtained at each startup to eliminate influences caused by changes of the environment around the aspirating tube 6a, 7a, 8a.

Figure 7:
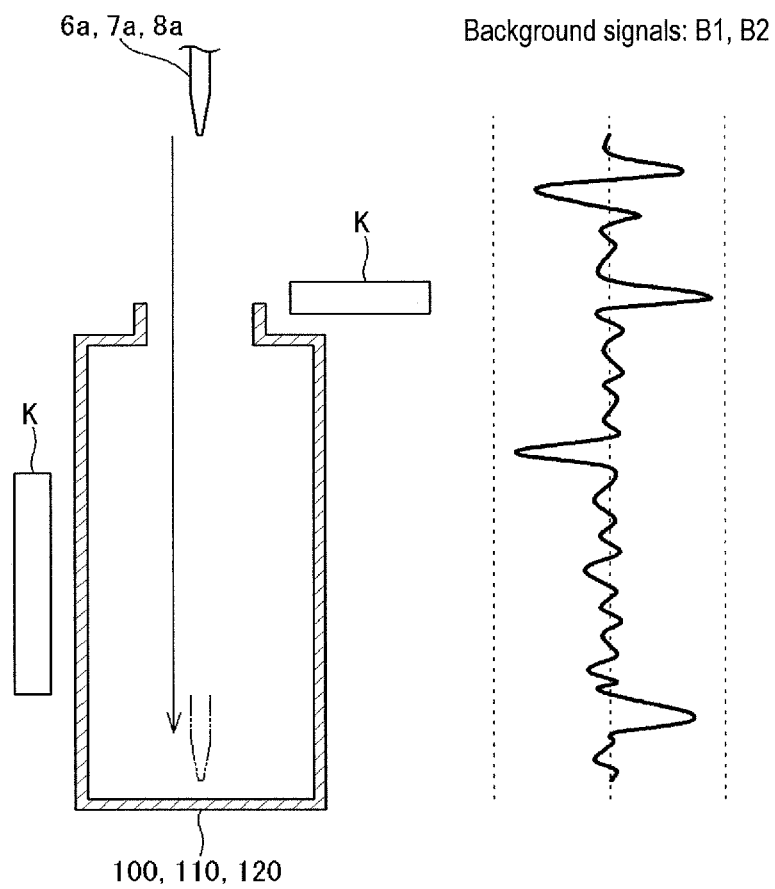
FIG. 7 illustrates changes of background signal measured at vertical positions of the aspirating tube.

As shown in FIG. 7, conductors K such as metal panels and the like are present around the reagent containers 100, 110, 120. Reagent is not present in the reagent container 100, 110, 120. The graph shown on the right side of the drawing shows the output signal from the capacitance detector 21 obtained when the aspirating tube 6a, 7a, 8a travels vertically in this situation. The output signal fluctuates greatly when the aspirating tube 6a, 7a, 8a approaches the conductor K and moves away from the conductor K. The output signal also fluctuates greatly upon an acceleration of the velocity that takes place when the aspirating tube 6a, 7a, 8a starts to move downward from a higher stopped position.

Figure 8:
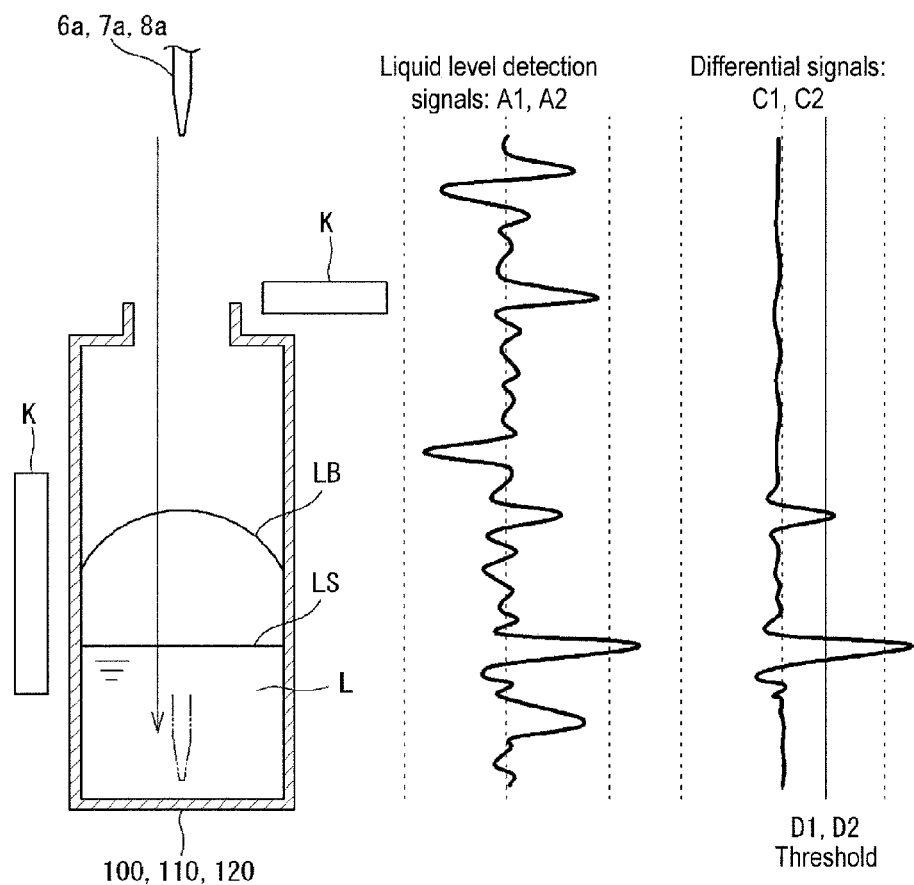
FIG. 8 illustrates changes of liquid level detection signal measured at vertical positions of the aspirating tube and its differential signal.

As shown in FIG. 8, the reagent L is contained in the reagent container 100, 110, 120, and can be aspirated by the aspirating tube 6a, 7a, 8a. The graph in the center of the figure shows the output signal from the capacitance detector 21 obtained when the aspirating tube 6a, 7a, 8a is moved vertically in this situation. The output signal fluctuates greatly at instances, for example, where the aspirating tube 6a, 7a, 8a accelerates its move, where the aspirating tube 6a, 7a, 8a make a contact with the reagent L, and where the aspirating tube 6a, 7a, 8a approaches a nearby conductor K and moves away from the nearby conductor K.

Given the relationship between the background signal of FIG. 7 and the liquid level detection signal, it becomes possible to discern the change of the liquid level detection signal that takes place only at the instance where a contact is made with the reagent L. Specifically, only the signal indicative of a contact with the reagent L can be discerned by the background signal from the liquid level detection signal. A graph representing the differential signal is shown on the right side in FIG. 8. In the graph, the changes that take place when the aspirating tube 6a, 7a, 8a approaches and moves away from the nearby conductors K, and the changes that take place when the aspirating tube 6a, 7a, 8a is accelerating are canceled, and the only the signal that represents a contact of the aspirating tube with the reagent L in the reagent container 100, 110, 120 remains.

A bubble or membrane (the term "bubble" will be used to indicate both hereinafter) LB produced during transport or the like may be present in the reagent container 100, 110, 120. The capacitance changes when the aspirating tube 6a, 7a, 8a makes a contact with the bubble LB. In the graph showing the differential signal, it is to be understood that the differential signal changes not only when a contact is made with the liquid surface LS of the reagent, but also when a contact is made with the bubble LB.

A change in the differential signal which takes place at a contact with the bubble LB is difficult to discern from a change in the differential signal which takes place at a contact with the liquid surface LS. The present embodiment provides a measure to discriminate between the change that takes place when the aspirating tube 6a, 7a, 8a makes a contact with the liquid surface LS and the change that takes place when the tube makes a contact with the bubble LS. Specifically, the memory 23 of the liquid level detecting unit 20 stores an estimated level of the liquid surface LS of the reagent L beforehand. Then, when the differential signal between the background signal and the liquid level detection signal changes, it is determined whether or not the aspirating tube 6a, 7a, 8a has made a contact with the liquid surface LS by comparing the position of the aspirating tube 6a, 7a, 8a and an estimated level of the liquid.

The specific control sequences of acquiring the background signal and detecting a reagent liquid level mentioned above are described below in detail with reference to FIGS. 9 through 11. Note that in FIGS. 9 through 11, the term the "background signal" is abbreviated to the "BG signal."

[Background Signal Acquisition]

The reagent containers 100, 110 and 120, which are empty or contain a reagent below the dead volume is installed by a service person at predetermined positions on the inner table 162 and the outer table 163 of the reagent installation section 16.

Figure 9:
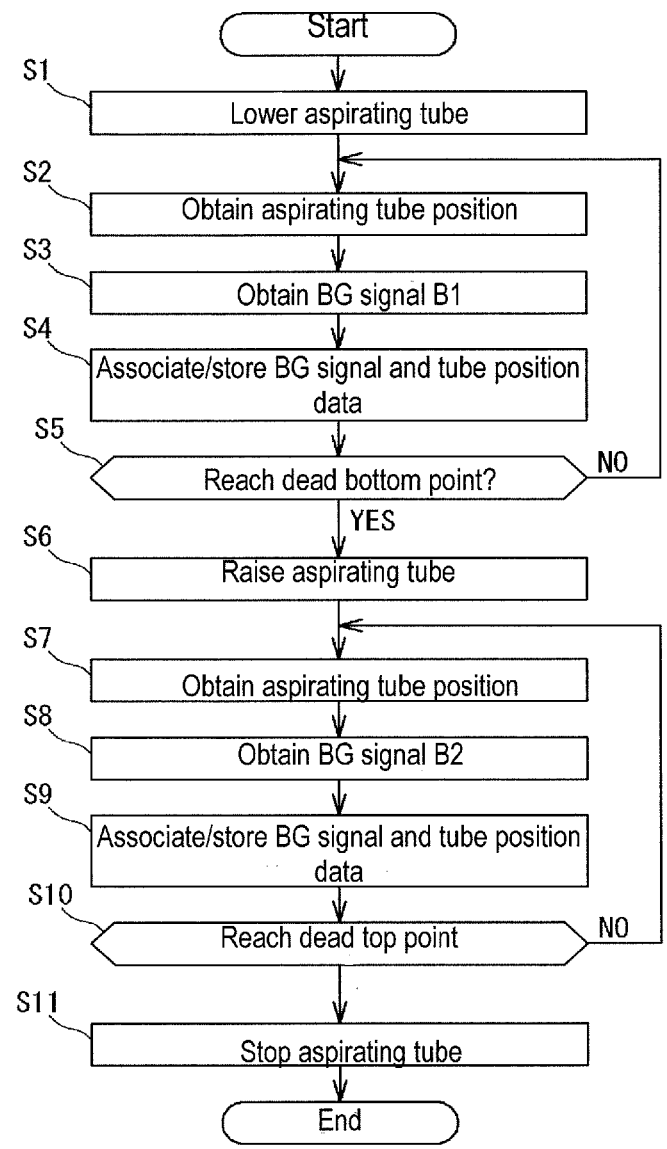
FIG. 9 is a flow chart showing a procedure for obtaining the background signal.

As shown in FIG. 9, the controller 22 controls the drive unit 60 to lower a respective one of the aspirating tubes 6a-8a when the immunoanalyzer 1 is switched on (step S1).

The controller 22 obtains the position of the aspirating tube 6a, 7a, 8a in the vertical direction from the position detector 65 (step S2), and obtains the output signal of the capacitance detector 21 as the background signal B1 (step S3).

The controller 22 associates the background signal B1 with the positions of the aspirating tube 6a, 7a, 8a in the vertical direction, and stores the data in the memory 23 (step S4).

The controller 22 then determines whether the aspirating tube 6a, 7a, 8a has arrived at the dead bottom point (step S5). The dead bottom point is set at a position near but not touching the bottom of the reagent container 100, 110, 120 installed in the reagent installation section 16. The process returns to step S2 when the aspirating tube 6a, 7a, 8a has not arrived at the dead bottom point, and the process advances to step S6 when the aspirating tube 6a, 7a, 8a has reached the dead bottom point.

In step S6, the controller 22 raises a respective one of the aspirating tubes 6a-8a, and obtains a background signal B2 and the position of the aspirating tube 6a, 7a, 8a in the vertical direction (steps S7, S8). The controller 22 associates the background signal B2 with the positions of the aspirating tube 6a, 7a, 8a in the vertical direction, and stores the data in the memory 23 (step S9). The controller 22 repeats steps S7 through S9 until a respective one of the aspirating tubes 6a-8a has arrived at the dead top point, and the process of stopping the aspirating tubes 6a-8a ends (step S11) when the controller 22 determines that the aspirating tubes 6a-8a have all reached the top dead point (step S10).

As described above, the background signals B1 and B2 are obtained, respectively, when the aspirating tubes 6a-8a are lowered and raised and stored in memory 23.

Note that the background signals B1 and B2 as described above are obtained for each of the reagent dispensers 6-8 containing the reagents R1-R3, respectively. The background signals B1 and B2 peculiar to each of the reagent dispensers 6-8 are obtained.

When the background signals B1 and B2 obtained by the controller 22 differ significantly from the background signals already stored in the memory 23 (for example, when the difference between the former and the latter exceeds a predetermined threshold value), an occurrence of an anomaly is suspected which may, for example, be a major change of the environmental surrounding the aspirating tubes 6a-8a, or a defect of the circuit or sensor in the system for obtaining the background signals. When an occurrence of an anomaly is suspected, the controller 22 notifies the control device 4, which may show an error message on the display/input section 410, and alert the user with a sound or light warning using a warning part.

[Reagent Aspiration Operation]

Figure 10:
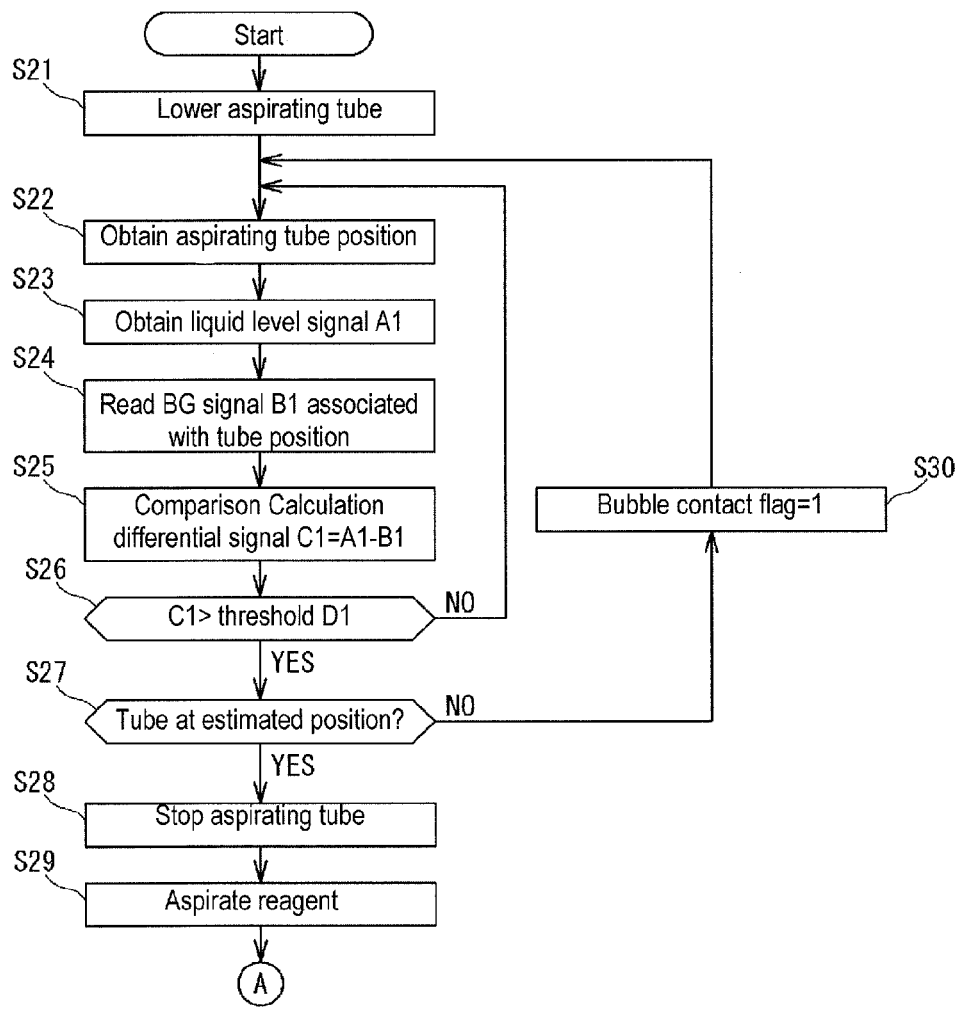
FIG. 10 is a flow chart showing a control sequence of the reagent aspirating operation by the aspirating tube.
Figure 11:
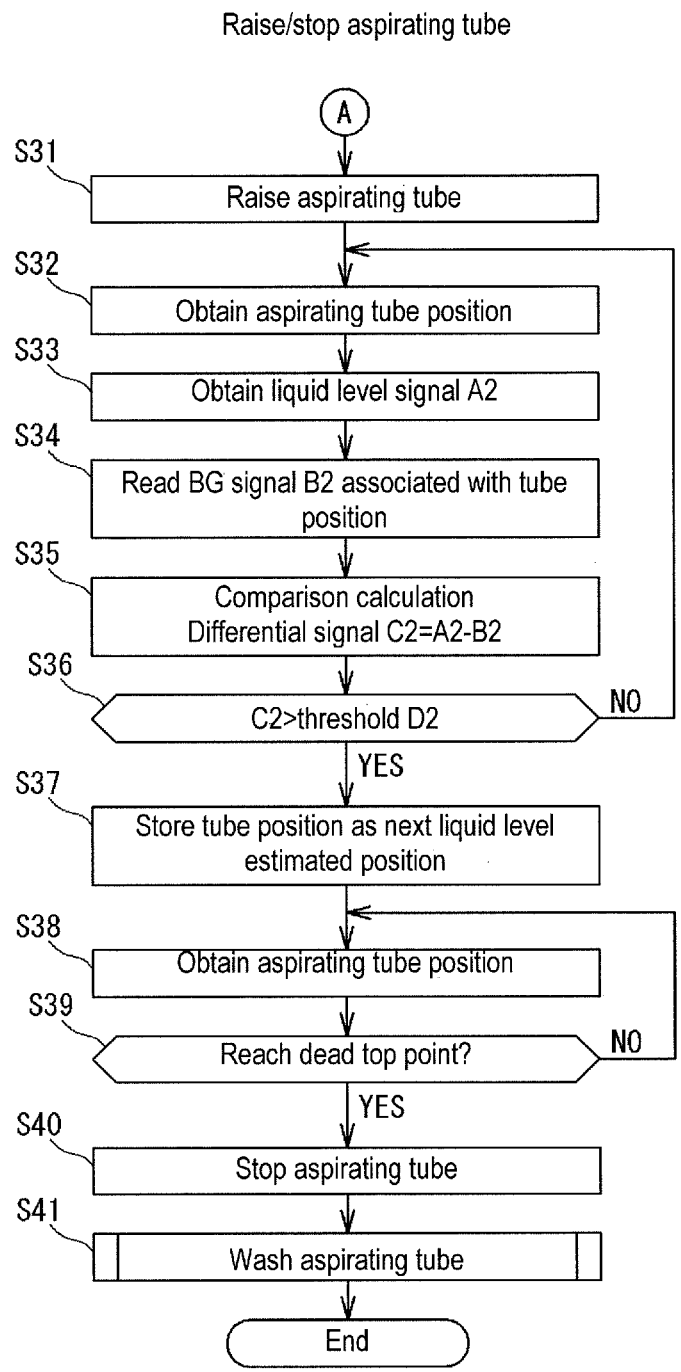
FIG. 11 is a flow chart showing a control sequence of the reagent aspirating operation by the aspirating tube.

As shown in FIGS. 10 and 11, the controller 22 controls the drive unit 60 to lower the aspirating tube 6a, 7a, 8a (step S21). The position of the aspirating tube 6a, 7a, 8a in the vertical direction is obtained from the position detector 65 (step S22), and the output signal of the capacitance detector 21 is obtained as a liquid level detection signal A1 (step S23).

The controller 22 reads from the memory 23 the background signal B1 exhibited by the aspirating tube 6a, 7a, 8a at the same position (step S24) and subtract the background signal B1 from the liquid level detection signal A1 to derive a differential signal C1 (C1=A1−B1) (step S25). The differential signal C1 obtained at this time is such as the one shown in the graph on the right side of FIG. 8.

The controller 22 determines whether the differential signal C1 is greater than a predetermined threshold value D1 (refer to FIG. 8) (step S26), and the process returns to step S22 when the signal C1 is less than the threshold D1, and the process advances to step S27 when the signal C1 is greater than or equal to the threshold D1.

In step S27, the controller 22 determines whether the aspirating tube 6a, 7a, 8a is situated at an estimated level of the liquid surface LS. The estimated level is obtained in step S37 and will be described below. When step S27 is executed for the first time, since the estimated level is not yet obtained, a level of the liquid surface estimated from the capacity of the reagent container 100, 110, 120, which is newly installed in reagent installation section 16, is, for example, set as an estimated level, and stored in the memory 23.

Although the estimated level of the liquid surface LS may be a value indicative of a vertical position, a predetermined vertical range (for example, a range of about 1 mm) may be set as the value in the present embodiment. When the position of the tip of the aspirating tube 6a, 7a, 8a becomes equal to the estimated level of the liquid, or falls within the predetermined range, the position is determined to be the liquid surface LS of the reagent L, and the process advances to step S28. When the position of the tip of the aspirating tube 6a, 7a, 8a is not equal to the estimated level of the liquid, the process advances to step S30, and then returns to step S22.

The controller 22 stops lowering the aspirating tube 6a, 7a, 8a in step S28, and suctions the reagent L in the reagent container 100, 110, 120 in step S29. The aspirating operation of the reagent L includes an operation of lowering the aspirating tube 6a, 7a, 8a only for a predetermined distance from the detected level of the reagent L. This predetermined distance is equal to a distance which allows the aspirating tube 6a, 7a, 8a to remain in the liquid even after the liquid surface LS lowers by an aspiration of the reagent L.

On the other hand, in step S30, the controller 22 sets the bubble contact flag to a value of "1". In step S26, when the differential signal C1 is determined to be greater than the predetermined threshold value D1, the aspirating tube 6a, 7a, 8a is considered to have made a contact with the liquid surface LS of the reagent L or a contact with the bubble LB above the liquid surface LS. In step S27, when the position of the tip of the aspirating tube 6a, 7a, 8a is not equal to the estimated level of the liquid, it is probable that the aspirating tube 6a, 7a, 8a has made a contact with the bubble LB. Therefore, in this case, the aspirating tube 6a, 7a, 8a is determined to have made a contact with the bubble LB, and the bubble contact flag is raised. Note that the bubble contact flag is also used when the aspirating tube 6a, 7a, 8a is washed after a reagent aspiration in step S41, which is described below.

The controller 22 then raises the aspirating tube 6a, 7a, 8a (step S31), obtains the vertical position of the aspirating tube 6a, 7a, 8a from the position detector 65 (step S32), and obtains the output signal of the capacitance detector 21 as a liquid level detection signal A2 (step S33).

The controller 22 reads from the memory 23 the background signals B2 exhibited by the aspirating tube 6a, 7a, 8a at the same position (step S34), subtracts the background signal B2 from the liquid level detection signal A2 to derive a differential signal C2 (C1=A2−B2) (step S35). The differential signal C2 obtained at this time is such as the one shown in the graph on the right side of FIG. 8.

The controller 22 determines whether the differential signal C2 is greater than a predetermined threshold value D2 (step S36), and the process returns to step S32 when the signal C2 is less than or equal to the threshold D2, and the process advances to step S37 when the signal C2 is greater than the threshold D2.

In step 37, when the differential signal C2 is greater than the threshold value D2, the controller 22 stores in memory 23 the position of the aspirating tube 6a, 7a, 8a as a next estimated level of the liquid to be used.

Thereafter, the controller 22 obtains the position of the aspirating tube 6a, 7a, 8a (step S38), determines whether the aspirating tube 6a, 7a, 8a has reached the top dead point (step S39), and stops raising the aspirating tube 6a, 7a, 8a when the tube has reached the top dead point (step S40).

Thereafter, a washing process of the aspirating tube 6a, 7a, 8a is executed (step S41), and the process ends.

[Aspiration Tube Washing Unit Structure and Operating Sequence]

The aspirating tube washing process of step S41 in FIG. 11 is described in detail below.

The structure of the measuring section 2 according to the present embodiment is described above; however, an aspiration tube washing unit 220 is also provided to wash the aspirating tubes 6a-8a after a reagent is aspirated and then discharged. The aspirating tube washing unit 220 has a wash container 221, and the wash container 221 has a washing orifice 222 through which the aspirating tube 6a, 7a, 8a is inserted, and a washing nozzle 223 which discharges a washing liquid into the wash container 221. The wash container 221 is arranged within the range of movement of the aspirating tubes 6a through 8a.

The washing orifice 222 is an opening formed on the top end of the wash container 221, and the aspirating tubes 6a-8a can be inserted from this opening. The washing nozzle 223 is configured to wash the aspirating tubes 6a-8a by discharging the washing liquid obliquely from the above through the washing orifice 222, and spraying the washing liquid on the aspirating tubes 6a-8a inserted in the washing orifice 222. A range of the aspirating tubes 6a-8a to be washed can be changed by changing the depth at which the aspirating tubes 6a-8a are inserted through the washing orifice 222.

Figure 12:
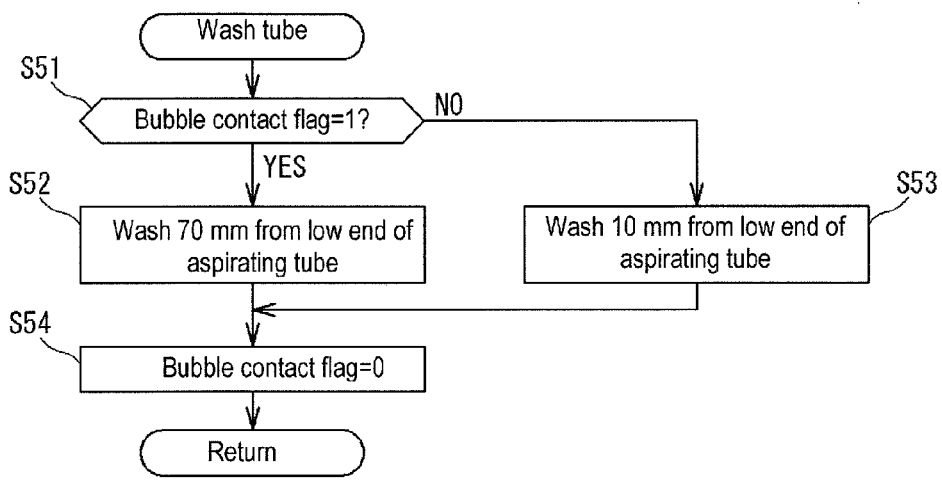
FIG. 12 is a flow chart showing a control sequence of the aspirating tube washing process.
Figure 13:
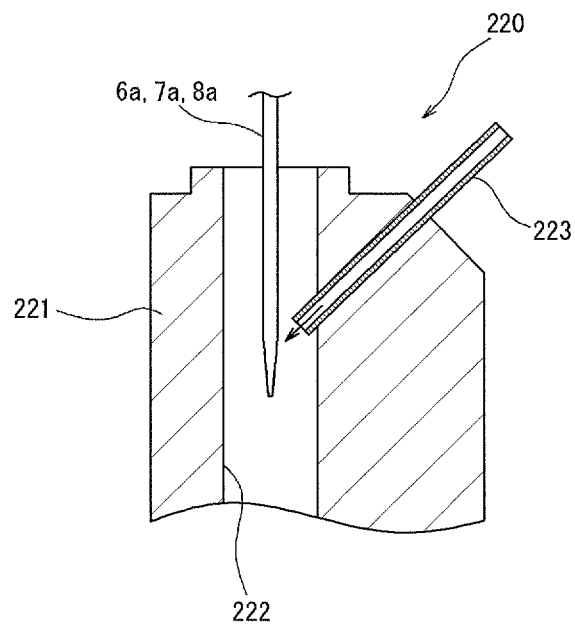
FIG. 13 is a cross sectional view of the aspirating tube washing unit.

The aspirating tube washing process of step S41 of FIG. 11 is described below referring to FIG. 12.

The controller 22 determines whether the bubble contact flag obtained in step 30 of FIG. 10 is set to a value of "1" (step S51).

The process advances to step S52 when the bubble contact flag is set to a value of "1", and the process continues to step S53 when the flag is not set to a value of "1".

Since it is probable that the aspirating tube 6a, 7a, 8a has made a contact with the bubble LB when the bubble contact flag is set to a value of "1" as previously described, the tip of the aspirating tube 6a, 7a, 8a makes a contact with the reagent L in a relatively broad range thereof. Therefore, when the bubble contact flag is set to a value of "1", a wider range of 70 mm measured from the bottom end of the aspirating tube 6a, 7a, 8a is washed in step S52. When the bubble contact flag is not set to a value of "1", a narrower range of 10 mm measured from the bottom end of the aspirating tube 6a, 7a, 8a is washed in step S53. In this way, the aspirating tubes 6a through 8a are reliably washed even when a contact has been made with the bubble, and cross-contamination is prevented.

In step S54, the controller 22 initializes the bubble contact flag to a value of "0" and the process ends.

Note that the specific numerical values of the washing range of the aspirating tubes 6a through 8a are examples, and the present invention is not limited to these values. When the bubble contact flag is set to a value of "1" as described previously, a signal may be sent to the control device 4 to display a message in the control device 4 indicating that the aspirating tube 6a, 7a, 8a has made a contact with the bubble.

Since the liquid level is detected by the liquid level detecting unit 20 when the reagent L is aspirated from the reagent container 100, 110, 120 in the present embodiment described above, the aspirating tubes 6a-8a can be reliably inserted into the reagent L for aspiration, and the aspirating tubes 6a-8a can be inserted into the reagent L at a minimum depth, and cross-contamination can be prevented.

Since the liquid level detecting unit 20 detects the liquid surface LS of the reagent L based on the liquid level detection signals (real signals) A1 and A2 and the background signals (reference signals B1 and B2) stored in memory 23, the liquid surface LS of the reagent L can be accurately detected by excluding the influences caused by conductors K present around the reagent containers 100, 110 and 120, influences caused by changes of the moving speed of the aspirating tube 6a, 7a 8a, and the influence caused by loosened metal screws and replaced metal parts around the containers. Because the influence caused by changes of the moving speed of the aspirating tube 6a, 7a, 8a is eliminated, the aspirating tubes 6a-8a can operate at a higher speed and the measurement cycle time can be reduced.

The liquid level detecting unit 20 correctly detects whether the aspirating tube 6a, 7a, 8a has made a contact with the liquid surface LS or made a contact with the bubble LB by using the estimated level of the liquid surface LS of the reagent L. An erroneous aspiration of reagent L therefore is prevented which may take place when the bubble LB is mistakenly detected as the liquid surface LS.

The measuring section 2 of the present embodiment can reliably prevent cross-contamination because the liquid level detecting unit 20 detects whether the aspirating tube 6a, 7a, 8a makes contact with the bubble LB, and a wide range of the aspirating tube 6a, 7a, 8a is washed when the aspirating tube has made a contact with the bubble LB.

Note that the present invention is not limited to the above described embodiment and may be modified within the scope of the claims.

For example, although the reagent containers, which are empty or contain reagents below the dead volume, are installed in the container holders of the reagent installation section in order to obtain the background signals, the reagent containers need not be installed inasmuch as the background signal also may be obtained when the reagent container is not installed. However, an accurate background signal can be obtained when the reagent containers are installed.

Although the background signal is automatically obtained each time the immunoanalyzer 1 is switched on in the above embodiment, the present invention is not limited to this. For example, the background signal can be automatically obtained and stored in memory 23 when the reagent container 100, 110, 120 is empty, or the liquid L in the reagent container 100, 110, 120 is below the dead volume. In this case, for example, step S37 of FIG. 11 includes an operation of storing the estimated level and an operation of determining whether the stored estimated level is lower than the liquid level of the reagent in the container which is at the dead volume. Upon a determination that the estimated level is lower than the liquid level of the reagent in the container which is at the dead volume, the background signal acquisition process shown in FIG. 9 is triggered to start.

Although the liquid level detecting unit described above detects the liquid level of the reagent contained in a reagent container, the liquid level detecting unit may also be used to detect the liquid level of a sample held in a sample container.

Although the control device according to the above embodiment is integrated with a measuring section, the control device also may be provided as a stand alone personal computer or the like.

Although in the above embodiment, the background signal in the device is obtained and stored in memory when the immunoanalyzer is switched on, when the reagent container is empty, or when the apparatus is manufactured or installation, the background signal also obtained from a separate immunoanalyzer, for example, a prototype or a master device, may be used.

Although in the above embodiment, the present invention is discussed using the immunoanalyzer 1 as an example of an analyzer in which the present invention is practiced, the present invention is not limited to the embodiment. For example, the present invention also is applicable to other clinical analyzers such as a blood coagulation measuring apparatus, a multi item blood cell analyzer, a urine component analyzer, a gene amplification measuring apparatus and the like.

Although the output signal of the capacitance detector is associated with the vertical positions of the aspirating tube 6a, 7a, 8a and stored as the reference signal representing a signal for the moving aspirating tube, the present invention is not limited to the embodiment. For example, the output signal also may be stored in association with time durations each measured from the time the aspirating tube 6a, 7a, 8a begins its movement, or the output signal may be stored in association with distances at which the aspirating tube 6a, 7a, 8a travels.

Although an electrostatic capacity sensor is used as the capacitance detector 21 in the above embodiment, the detector is not specifically limited as long as the capacitance detector 21 can detect changes in the physical characteristics indicating relationship between the aspirating tube and its environment surrounding the aspirating tube including the liquid level of the liquid in a liquid container. For example, in addition to an electrostatic capacity sensor, a voltage sensor, a ultrasonic sensor, an electrical resistance sensor or the like may be used as the capacitance detector 21.

What is claimed is:

1. An analyzer comprising:
   a reagent installation section in which a container is installable, the container being storable of a liquid inside;
   an aspirating tube operable to travel up-and-down in the container to aspirate the liquid from the container installed in the reagent installation section;
   a drive part configured to drive the aspirating tube to travel up-and-down in the container;
   a detector configured to detect a change of a physical property of the aspirating tube attributable to an interaction between the aspirating tube and environmental objects surrounding the aspirating tube; and
   a controller programmed to operate the drive part to drive the aspirating tube to travel up-and-down and read detection signals from the detector during descending or ascending of the aspirating tube, the controller having a memory configured to that stores first detection signals obtained from the detector during a first operation including descending or ascending the aspirating tube in an environment exclusive of the liquid,
   the controller further programmed to:
   perform a second operation for operating the drive part to drive the aspirating tube to descend inside the container containing the liquid;
   subtracting the first detection signals from second detection signals from the detector during the second operation, and
   identify a change of the second detection signals attributable to a contact of the aspirating tube with a surface of the liquid in the container to detect a liquid level of the liquid position in the container.

2. The analyzer of claim 1, wherein the controller is programmed to perform the first operation, the first operation including:
   operating the drive part to drive the aspirating tube to descending or ascending; and
   obtaining the first detection signals from the detector.

3. The analyzer of claim 1, wherein the controller is programmed to:
   compare a difference between the second detection signals and the first detection signals with a first predetermined threshold; and
   upon a determination that the difference exceeds the first predetermined threshold, identify a change in the second detection signals as the change attributable to a contact of the aspirating tube with the surface of the liquid in the container.

4. The analyzer of claim 3, further comprising a position sensor configured to detect height positions of the aspirating tube while the aspirating tube is descending or ascending, wherein the controller is programmed to:
   find a first detection signal, which is derived at a height position of the aspirating tube detected by the position sensor at which the second detection signal is obtained; and
   determine the level of the liquid in the container from a height position of the aspirating tube detected by the position sensor at which the difference between the second detection signal and the first detection signal exceeds the first predetermined threshold.

5. The analyzer of claim 4, wherein
   the memory is storable of a range of an estimated level of the liquid, and
   the controller is programmed to identify a change of the second detection signal as the change attributable to a contact of the aspirating tube with the surface of the liquid in the container only when the change occurs within the range of estimated level.

6. The analyzer of claim 5, further comprising a washer configured to wash a length from a tip of the aspirating tube wherein the controller is programmed to operate the washer to:
   wash the aspirating tube at a first length subsequent to a determination by the controller that the difference between the second detection signal and the first detection signal exceeds the first predetermined threshold outside the range of estimated level of the liquid; and
   wash the aspirating tube at a second length subsequent to a determination by the controller that the difference between the second detection signal and the first detection signal exceeds the first predetermined threshold within the range of estimated level of the liquid, wherein the first length is longer than the second.

7. The analyzer of claim 6, further comprising a display, wherein the controller is programmed to show bubble detection information on the display responsive to a determination by the controller that the difference between the second detection signal and the first detection signal exceeds the first predetermined threshold outside the range of estimated level of the liquid.

8. The analyzer of claim 5, wherein the controller is further programmed to perform a third operation for:
   operating the drive part to drive the aspirating tube to ascend inside the container; and
   subtract the first detection signals from third detection signals obtained form the detector during the third operation, and
   identify a change of the third detection signals attributable to a separation of the aspirating tube from the surface of the liquid in the container.

9. The analyzer of claim 8, wherein the controller is programmed to:
   compare a difference between the third detection signal and the first detection signal with a second predetermined threshold; and
   upon a determination that the difference between the third detection signal and the first detection signal exceeds the second predetermined threshold, identify a change of the third detection signal as the change attributable to a separation of the aspirating tube from the surface of the liquid in the container.

10. The analyzer of claim 9, wherein the position sensor is configured to detect a height position of the aspirating tube while the aspirating tube is ascending, and the controller is programmed to:
    find the first detection signal, which is obtained at a height position of the aspirating tube detected by the position sensor at which the third detection signal is obtained;
    determine the level of the liquid in the container from a height position of the aspirating tube detected by the position sensor at which a difference between the third detection signal and the first detection signal exceeds the second predetermined threshold; and
    derive the range of estimated level of the liquid from the determined level.

11. The analyzer of claim 1, wherein the controller is programmed to perform the first operation when the container is empty of the liquid or contains the liquid below a dead volume.

12. The analyzer of claim 2, wherein the controller is programmed to perforin the first operation each time the analyzer is switched on.

13. The analyzer of claim 2, wherein the controller is programmed to perform the first detection each time the container becomes empty or the liquid in the container becomes below a dead volume.

14. The analyzer of claim 1, wherein the controller is programmed to compare latest first detection signals stored in the memory with previously obtained first detection signals stored in the memory and warn a user in response to a determination by the controller that a difference between the latest first detection signals the previously obtained first detection signals exceeds a third threshold value.

15. The analyzer of claim 1, comprising a plurality of aspirating tubes including the aspirating tube, and the controller is programmed to store in the memory the first detection signals relation to each aspirating tube.

16. The analyzer of claim 1, comprising a container containing a liquid installed in the reagent installation section, wherein the liquid is either a sample supplied to the analyzer, or a reagent used in analysis of the sample by the analyzer.

17. The analyzer of claim 1, wherein the detector is configured to detect a change of an electrostatic capacity of the aspirating tube attributable to an interaction between the aspirating tube and the environmental objects inclusive of the liquid in the container.

18. The analyzer of claim 1, wherein the liquid is a reagent for use in analysis by the analyzer, the analyzer further comprising a preparation portion configured to prepare a measurement sample from the reagent and a sample, and a measurement portion configured to measure an analyte contained in the measurement sample.

* * * * *

UNITED STATES PATENT AND TRADEMARK OFFICE
CERTIFICATE OF CORRECTION

PATENT NO. : 9,733,115 B2
APPLICATION NO. : 14/665614
DATED : August 15, 2017
INVENTOR(S) : Takayuki Endo Page 1 of 1

It is certified that error appears in the above-identified patent and that said Letters Patent is hereby corrected as shown below:

In the Claims

In Column 15, Claim 1, Line 24, after "having a memory" delete "configured to".

In Column 15, Claim 1, Line 37, after "to detect a" delete "liquid".

In Column 15, Claim 1, Line 38, after "the liquid" delete "position".

In Column 16, Claim 6, Line 23, after "than the second" insert --length--.

In Column 17, Claim 12, Line 6, after "programmed to" replace "perforin" with --perform--.

In Column 17, Claim 13, Line 9, after "the first detection" insert --operation--.

In Column 18, Claim 15, Line 2, after "detection signals" insert --in--.

Signed and Sealed this
Fourteenth Day of August, 2018

Andrei Iancu
*Director of the United States Patent and Trademark Office*